(12) United States Patent
Kortsmit et al.

(10) Patent No.: US 8,609,415 B2
(45) Date of Patent: Dec. 17, 2013

(54) METHOD FOR MANUFACTURING A TISSUE-ENGINEERED CONSTRUCT

(75) Inventors: Jeroen Kortsmit, Cape Town (ZA); Niels Jozef Bart Driessen, Rosmalen (NL); Marcel Cornelis Maria Rutten, Eindhoven (NL); Franciscus Petrus Thomas Baaijens, Eindhoven (NL)

(73) Assignees: Technische Universiteit Eindhoven, Eindhoven (NL); Stichting Voor de Technische Wetenschappen, Utrecht (NL)

( * ) Notice: Subject to any disclaimer, the term of this patent is extended or adjusted under 35 U.S.C. 154(b) by 530 days.

(21) Appl. No.: 12/865,148

(22) PCT Filed: Feb. 2, 2009

(86) PCT No.: PCT/NL2009/000022
§ 371 (c)(1),
(2), (4) Date: Oct. 25, 2010

(87) PCT Pub. No.: WO2009/096780
PCT Pub. Date: Aug. 6, 2009

(65) Prior Publication Data
US 2011/0033885 A1 Feb. 10, 2011

(30) Foreign Application Priority Data
Feb. 1, 2008 (EP) .................................... 08001895

(51) Int. Cl.
*C12N 5/07* (2010.01)
*A61F 2/00* (2006.01)
*A01N 1/02* (2006.01)
*C12Q 1/02* (2006.01)
*C12N 11/00* (2006.01)
*C12M 3/00* (2006.01)

(52) U.S. Cl.
USPC .............. 435/395; 424/423; 435/1.1; 435/29; 435/174; 435/325; 435/284.1; 435/289.1

(58) Field of Classification Search
None
See application file for complete search history.

(56) References Cited

U.S. PATENT DOCUMENTS 5,899,937 A    5/1999  Goldstein et al.
8,394,632 B2 * 3/2013  Noll et al. ..................... 435/401

FOREIGN PATENT DOCUMENTS

EP    1 693 025      8/2006
WO    2006/030404   3/2006

* cited by examiner

Primary Examiner — David M Naff
(74) Attorney, Agent, or Firm — Barnes & Thornburg LLP (57) ABSTRACT

Method for manufacturing a tissue-engineered construct, such as a heart valve, comprising the steps of providing a-cell-seeded scaffold in a bioreactor chamber which bioreactor chamber is divided by the cell-seeded scaffold into a first compartment and a second compartment, subjecting the cell-seeded scaffold to a flow of nutrient medium within the bioreactor chamber for developing the cell-seeded scaffold to a tissue structure and next to the tissue construct, applying a dynamic pressure difference to the developing tissue structure by the flow of nutrient medium to induce dynamic strain on the tissue structure.

15 Claims, 8 Drawing Sheets

Figure 6b

METHOD FOR MANUFACTURING A TISSUE-ENGINEERED CONSTRUCT

This application is a national stage of International Application PCT/NL2009/000022, filed Feb. 2, 2009 and claims benefit of and priority to European Patent Application No. 08001895.5, filed Feb. 1, 2008, the content of which Applications is hereby incorporated by reference herein.

The present invention relates to a method for manufacturing a tissue-engineered construct, such as a heart valve.

EP 1 693 025 A1 discloses a bioreactor and a method for manufacturing tissue-engineered heart valves in which the developing heart valves are exposed to dynamic strains by applying a dynamic pressure difference over the leaflets of the heart valve.

A disadvantage of this known method is that the mechanical behaviour of heart valve tissue can only be evaluated by sacrificing the construct and consecutively performing tensile or indentation tests. As a consequence multiple heart valves need to be grown under identical conditions to obtain a second heart valve for example implantation still not knowing for sure that the properties of the heart valve which is implanted, are the same as the heart valve which is sacrificed for testing. Growing multiple heart valves makes the procedure more costly and does not guarantee that a second heart valve grown under similar conditions possesses the same mechanical properties as the tested valve.

A second drawback of this method and most current bioreactor systems is the lack of control during load application. Pressure is applied to the developing heart valve while deformations are unknown. They may alter during culturing as a result of changing mechanical properties of the tissue whereas the effects of variation in applied deformation on tissue remodeling are yet unknown.

A second method for developing heart valves is known froth U.S. Pat. No. 5,899,937. This method utilizes color Doppler flow mapping, spectral Doppler analysis, or laser Doppler anemometry to characterize the flow field near the aortic valve. These measurements can provide a estimate of the fluid velocity, from which the shear stress can be calculated. This method further utilizes videography to determine the opening and closing characteristics of the valve. In this method aortic pressure and the pressure drop across the valve are recorded and used to verify that each valve experiences similar flow conditions. A downside of this method is that the quality of the valve as far as mechanical properties are concerned can only be determined in a destructive and/or invasive manner.

The present invention aims in solving the above problems and provides a method comprising the steps of:

providing a cell-seeded scaffold in a bioreactor chamber which bioreactor chamber is divided by the cell-seeded scaffold into a first compartment and a second compartment, subjecting the cell-seeded scaffold to a flow of nutrient medium within the bioreactor chamber for developing the cell-seeded scaffold to a tissue structure and next to the tissue construct, applying a dynamic pressure difference to the developing tissue structure by the flow of nutrient medium to induce dynamic strain on the tissue structure measuring the dynamic pressure difference.

measuring the volumetric deformation of the developing tissue structure, determining the magnitude of at least one mechanical property of the tissue structure from the measured volumetric deformation and from applied pressure difference over the tissue structure while the tissue structure is within the bioreactor chamber.

determining if the determined magnitude of at least one mechanical property exceeds a certain threshold value continuing the subjection of the tissue structure to the dynamic pressure differences to induce dynamic strains if the determined magnitude of at least one mechanical property does not exceed the threshold value, ending the subjection of the tissue structure to the dynamic pressure differences to induce dynamic strains if the determined magnitude of at least one mechanical property exceeds the threshold value.

These steps enable the accurate characterization and testing of the mechanical properties of a tissue construct (or a tissue structure developing to a tissue construct) such as cultured heart valve leaflets, in a realtime non-invasive and non-destructive manner. Furthermore it can be used to monitor tissue remodeling over time. These steps further allow for the use of a conditioning protocol for tissue engineering of tissue-engineered constructs such as heart valve replacements, in which the threshold value is a predetermined value which is used to indicate at least one mechanical property of the valve. Advantageously, this threshold value can relate to for example the quality of the valve to be used as an implant. Once the determined magnitude of the at least one mechanical property exceeds the threshold value, one could consider the tissue structure to have become a tissue-engineered construct. It is noted that the volumetric deformation is defined as the amount of nutrient medium exiting and subsequently reentering the second compartment of the bioreactor chamber in a single loading cycle.

According to a preferred embodiment of the present invention, the method comprises the step of determining local tissue strains from the measured volumetric deformation. The ability to determine the local tissue strain enables the systematical study of the effects of mechanical loading on tissue structure development.

According to a further preferred embodiment the method comprises the step of applying a numerical model to determine the magnitude of the at least one mechanical property of the tissue structure and/or the local tissue strains. The utilization of a numerical model allows for the determination of the mechanical properties of the developing tissue structure in a realtime non-invasive and non-destructive manner.

Another preferred embodiment of the present invention is a method according to the previous methods further comprising the step of changing the dynamic pressure difference depending on the local tissue strains as determined and/or depending on the magnitude of at least one mechanical property of the tissue structure as determined. This way the development of the tissue structure can be optimized.

Another preferred embodiment of the present invention is a method according to the previous methods further comprising the step of gradually increasing the dynamic pressure preferably to a maximum value between 10 kPa and 20 kPa, more preferably between 13 kPa and 17 kPa. This enhances the cell proliferation and functional tissue formation as a result of cyclic tissue straining of the developing construct.

Yet another preferred embodiment is characterized by the step of applying the dynamic pressure difference with a frequency between 0.1 Hz and 10 Hz and more preferably between 0.5 Hz and 3 Hz. This dynamic pressure difference induces local tissue strains to the valve at a frequency range resembling physiological values of the heart beat sequence.

The dynamic pressure difference is preferably applied for at least 6 days and more preferably for 16 to 28 days in order to allow the tissue structure to develop sufficiently.

Preferably the cell-seeded scaffold is subjected to a continues flow of nutrient medium at a speed between 2 ml/min and 6 ml/min to develop the cell seeded scaffold to the tissue structure. This step allows for the seeded cells to develop and to attach to the scaffold and for supplying the cells with fresh nutrients.

Preferably the continues flow of nutrient medium in the bioreactor chamber is applied for at least 3 days before a dynamic pressure difference is applied on the developing tissue structure.

Although not exclusively, the present invention is very suitable for manufacturing heart valves. Consequently according to a preferred embodiment, the tissue-engineered construct is a heart valve.

The dynamic pressure on tissue structure developing to a heart valve tissue is preferably applied in closed configuration of the heart valve (to be). This way proper measurements of the dynamic pressure difference and the volumetric deformation can take place. Using the method according to the present invention the valve remains in the closed configuration without opening. In heart valve tissue engineering, many bioreactors have been developed and almost all systems try to mimic physiological flow. These systems either apply mechanical loading in a wide physiological range, mimicking both systole as well as diastole, or are characterized by simulation of the systolic or opening phase of the cardiac cycle. However, the diastolic phase or closing phase represents the load bearing phase of the cardiac cycle, in which most strain is applied to the heart valve tissue. The positive effect of cyclic tissue straining on the developing construct has been demonstrated. It enhances cell proliferation and functional tissue formation. Furthermore, an increase in ultimate tensile strength and tissue stiffness is observed, compared to static control.

One may also benefit from the present invention in case human or animal donor tissue constructs should be tested for their mechanical properties. In this respect the present invention also relates to a method for testing a tissue construct, such as a heart valve, comprising the steps of     providing a tissue construct to be tested, preferably a heart valve in a closed configuration, in a bioreactor chamber which bioreactor chamber is divided by the tissue construct into a first compartment and a second compartment,     applying a dynamic pressure difference to the tissue structure to induce dynamic strain on the tissue structure,     measuring the dynamic pressure difference, and     measuring the volumetric deformation of the tissue construct,     determining the magnitude of at least one mechanical property of the tissue construct from the measured volumetric deformation and from the applied pressure difference over the tissue structure.

This way tissue constructs in general may be tested in a realtime non-invasive and non-destructive manner. This allows for a tissue construct to grow and develop into a valve which can readily be used as an implant without having to subject these valves to mechanical testing in or outside of the bio-reactor to assess its quality. This considerably decreases the risk of contaminating the valve prior to implantation. Contamination would make the valve unusable as an implant. Furthermore it is no longer necessary to use methods to measure mechanical properties of the valve in which the valve is sacrificed.

Preferably the method comprises the step of subjecting the tissue construct to a flow of medium within the bioreactor chamber for applying the dynamic pressure difference and/or by the step of determining the magnitude of at least one mechanical property of the tissue construct while the tissue construct is within the bioreactor chamber.

The present invention will be explained in more detail referring to the following figures.

FIGS. 3a and 3b show the measured and fitted (predicted) relationship between applied pressure differences and induced volumetric deformation of two cultured heart valve leaflets grown according to the conditioning protocol depicted in FIG. 1a.

Figure 2:
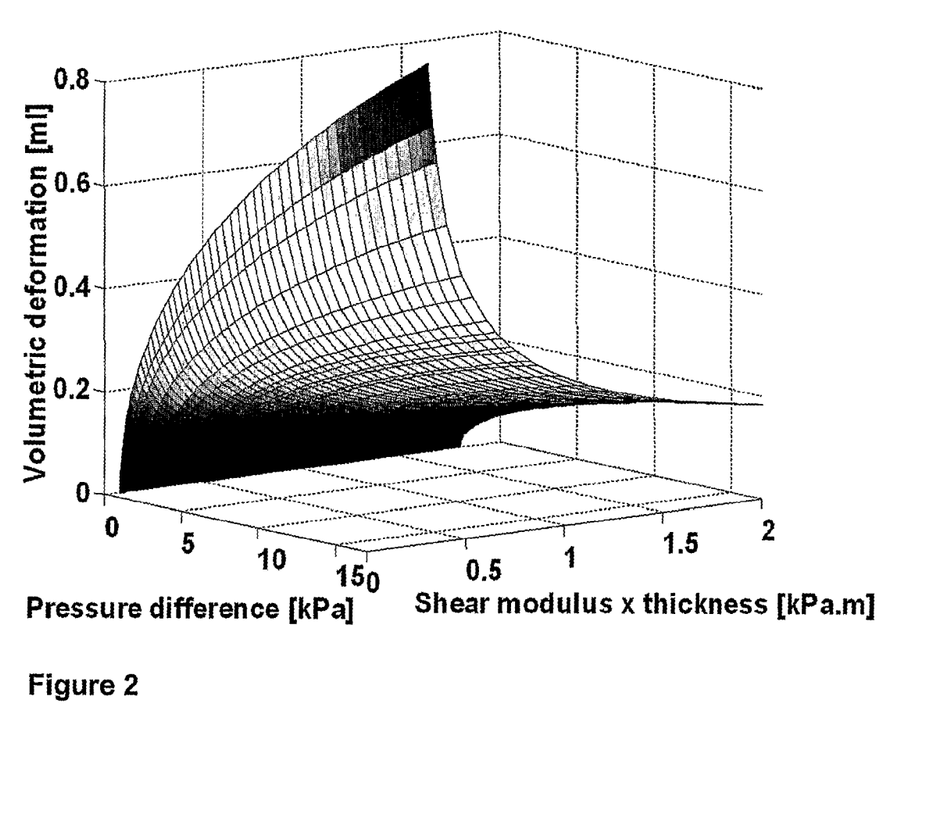
FIG. 2 shows a numerically obtained relation between the applied pressure difference, induced deformation and mechanical properties.

FIG. 2 shows a numerically obtained relation between the applied pressure difference [kPa] over the heart valve leaflets, induced deformation [ml] and mechanical properties [kPa·m], defined as shear modulus×thickness, of the valve.

To relate the combination of applied pressure and induced volumetric deformation of heart valve leaflets to the mechanical properties of the leaflets, a quasi-static numerical model of the heart valve is employed In the model, leaflets are assumed incompressible and therefore the total Cauchy stress ($\sigma$) is split into a hydrostatic pressure (p) and an extra stress ($\tau$):

$$\sigma = -pI + \tau \qquad (1)$$

To model non-linear mechanical behavior, a non-linear Neo-Hookean model is used:

$$\tau = G(B)(B-I), \qquad (2)$$

with the shear modulus G calculated from $$G(B) = G_0 (I_1(B)/3)^n \qquad (3)$$

with $G_0$ and n material parameters. $I_1(B) = \text{trace}(B)$ represents the first invariant of the left Cauchy-Green deformation tensor, which is calculated from $B = F \cdot F^T$, with F the deformation gradient tensor. The parameter n represents the degree of non-linearity of the constitutive equation: n>0 indicates stiffening of the material with increasing strains, whereas n<0 indicates softening.

The balance equations that have to be solved are conservation of momentum and mass for an incompressible solid:

$$\vec{\nabla} \cdot \sigma = \vec{v} \qquad (4)$$

$$J - 1 = 0 \qquad (5)$$

where $J = \det(F)$ represents the volume change between the undeformed, stress-free configuration and the deformed configuration.

The finite element mesh of the leaflets in the closed configuration is symmetric and therefore consists of only one half of a leaflet. At the symmetry edge, nodal displacements in the normal direction are suppressed. At the bottom (ventricular) side of the fixed edge, nodal displacements are suppressed in all directions. At the free edge, a contact surface is defined to model coaptation of adjacent leaflets. The radius of the leaflets is set to 12 mm here. Pressure is applied to the top surface of the leaflets to model the applied diastolic transvalvular load. Subsequently, volumetric deformations are calculated.

To obtain the 3D relationship between applied pressure, induced volumetric deformation and the mechanical properties of the loaded heart valve, simulations were conducted. The mechanical properties were defined as the product of thickness (t) and shear modulus (G) of the heart valve, and were used in different combinations as an input for the model. The range of these input parameters was chosen to cover experimental data from previous studies. Shear modulus (G) was varied between 0.1 and 2.0 MPa and thickness (t) between 0.35 and 1.0 mm. The degree of non-linear material behavior (n) of the heart valve was kept constant at n=10. For every combination of thickness and shear modulus, pressure differences, ranging from 0 to 15 kPa were applied to the valve and induced deformations were calculated. Hence, a 3D relation of these quantities was obtained. However, to acquire a 3D plot in which every pressure-deformation set will lead to one unique value for the mechanical properties, a surface was fitted through the simulation results.

EXAMPLE 1

Experiment 1 and 2

Cells were cultured and seeded onto a scaffold according to methods well known in literature. The cell-seeded scaffold provided in the bioreactor chamber is subjected to a continues flow of nutrient medium at a speed between 2 ml/min and 6 ml/min to develop the seeded scaffold to a tissue. Preferably the cell-seeded scaffold is subjected to a continues flow of nutrient medium in the bioreactor chamber for at least 3 days.

Figure 1:
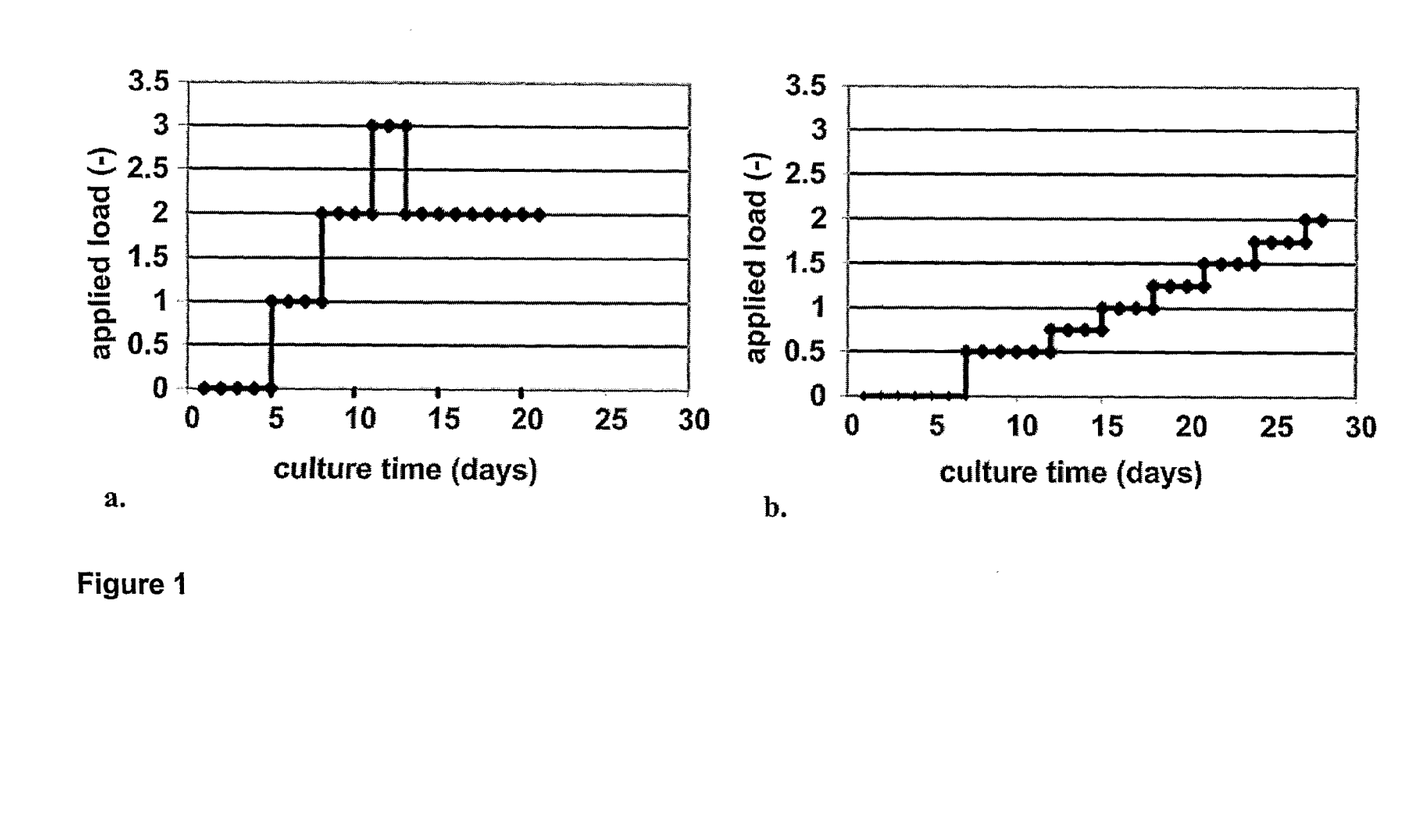
FIGS. 1a and 1b show two conditioning protocols.

Next, dynamic pressure differences at a frequency between 0.1 and 10 Hz were applied to the heart valve leaflets for at least 6 days and preferably from 16 to 21 days. Two conditioning protocols are shown in FIG. 1, in which the applied load is given as a function of culture time, for tissue engineered heart valves 1-1 and 1-2 (*a*) and valves 2-1 to 2-4 (*b*). In a first experiment (experiment 1), load was applied in steps for 9 days, increasing every 3 days. After those 9 days, the applied load was kept constant and heart valves (valves 1-1, 1-2) were sacrificed after a total culture time of 3 weeks (FIG. 1*a*). In a second experiment (experiment 2) pressure application was increased in 3-day steps until the end of the experiment. Heart valve culture was finished after 3 weeks (valves 2-2,2-4) and 4 weeks (valves 2-1,2-3) (FIG. 1*b*).

Figure 3:
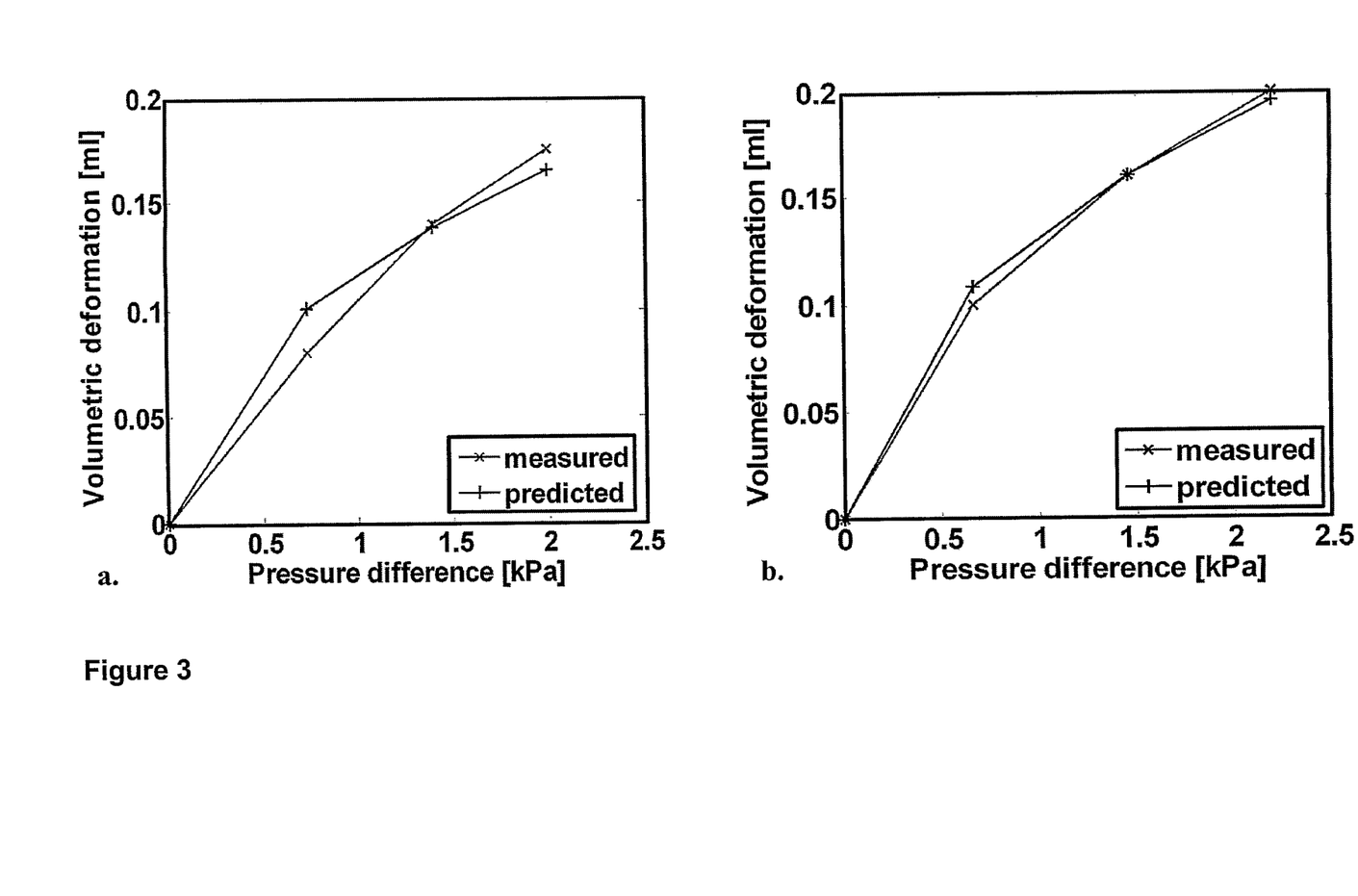

The measured and fitted (predicted) relationship, between applied pressure differences [kPa] and induced volumetric deformation [ml] of the cultured heart valve leaflets in the first experiment are depicted in FIGS. 3*a* and 3*b*. Data were obtained after 3 weeks of culture adjust before sacrifice for (3*a*) valve 1-1 and (3*b*) valve 1-2.

Figure 4:
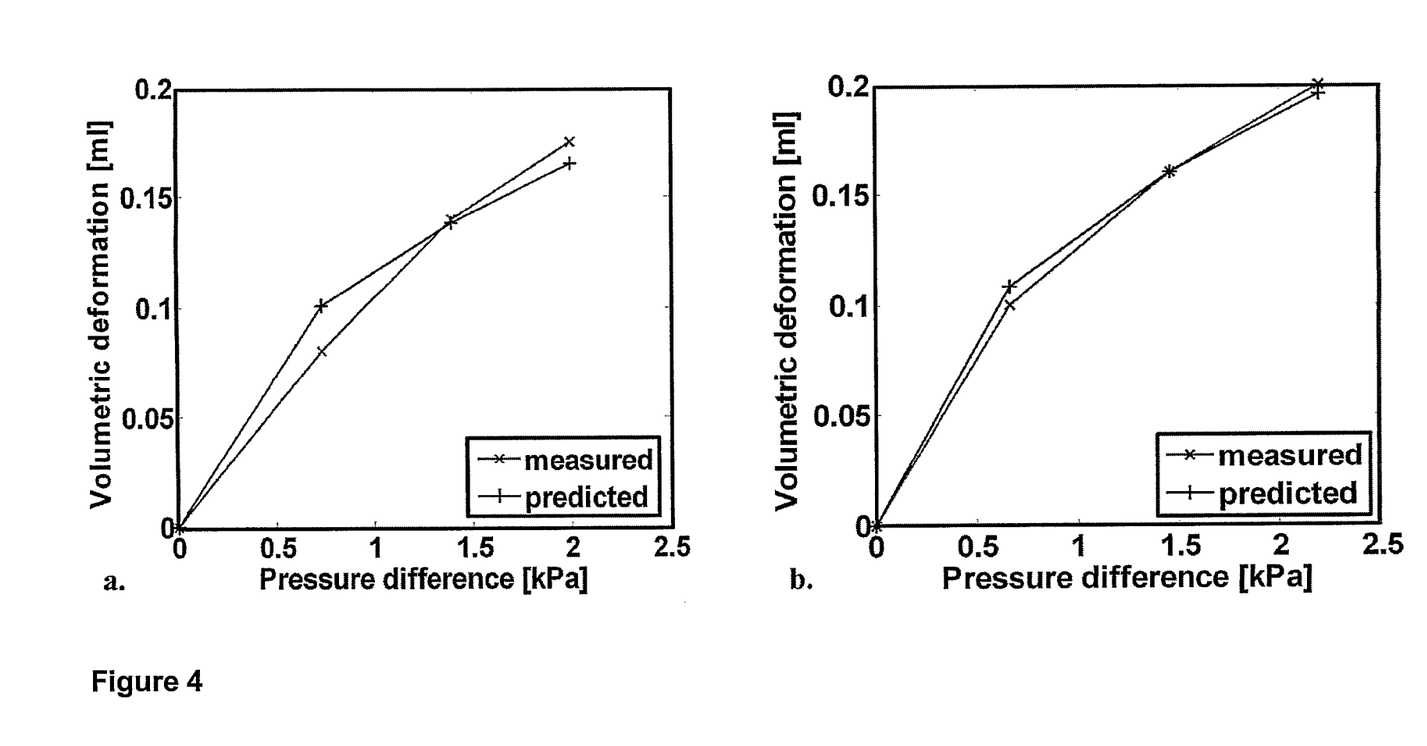
FIGS. 4a to 4d show the measured and fitted (predicted) relationship between applied pressure differences and induced volumetric deformation of four cultured heart valve leaflets grown according to the conditioning protocol depicted in FIG. 1b.

Measured and fitted (predicted) relationship between applied pressure differences [kPa] and induced volumetric deformation [ml] of the cultured heart valve leaflets in the second experiment are shown in FIG. 4. Data were obtained just before sacrifice after 3 weeks of culture for (4*b*) valve 2-2 and (4*d*) valve 2-4, and after 4 weeks of culture for (4*a*) valve 2-1 and (4*c*) valve 2-3.

Table 1 shows the relative leakage of the valves-(%-leak) and correlation values between the measured values of the actual heart valves and the estimated values according to the present invention. As can be seen in this table, a strong correlation exists between the measured and predicted values. Only in the case of valve 2-2 was the correlation less strong this was assigned to the high relative leakage of valve 2-2. During load application, flow measurements were performed to assess the volumetric deformation and leakage of the heart valve leaflets. Volumetric deformation was defined as the amount of fluid exiting and subsequently reentering the bioreactor at the second compartment side of the bioreactor in a single loading cycle. The net flow leaving the bioreactor from the second compartment was defined as the amount of fluid leaking through the valve.

This shows that the method for manufacturing a tissue-engineered prosthesis according to the present invention allows for the assessment of overall mechanical properties of tissue engineered heart valve leaflets, in real-time, non-invasively and nondestructively, during and after culturing. Therefore, the method can serve as a real-time noninvasive and non-destructive quality check.

TABLE 1

| Valve | %-leak | Correlation coefficient $R^2$ |
|---|---|---|
| 1-1 | 10 | 0.97 |
| 1-2 | 7 | 0.99 |
| 2-1 | 9 | 0.98 |
| 2-2 | 32 | 0.88 |
| 2-3 | 0 | 0.98 |
| 2-4 | 1 | 0.99 |

EXAMPLE 2

Experiment 3 and 4

After seeding the heart valve constructs were placed in the bioreactor system and subjected to culture medium circulation at low speed (4 ml/min) for 12 days to allow initial tissue development after seeding. Thereafter, dynamic pressure differences (at 1 Hz) were applied to the heart valve leaflets for 16 days. Total culture time included the application of (low speed) medium circulation as well as the application of dynamic loads to the engineered valves.

Figure 5:
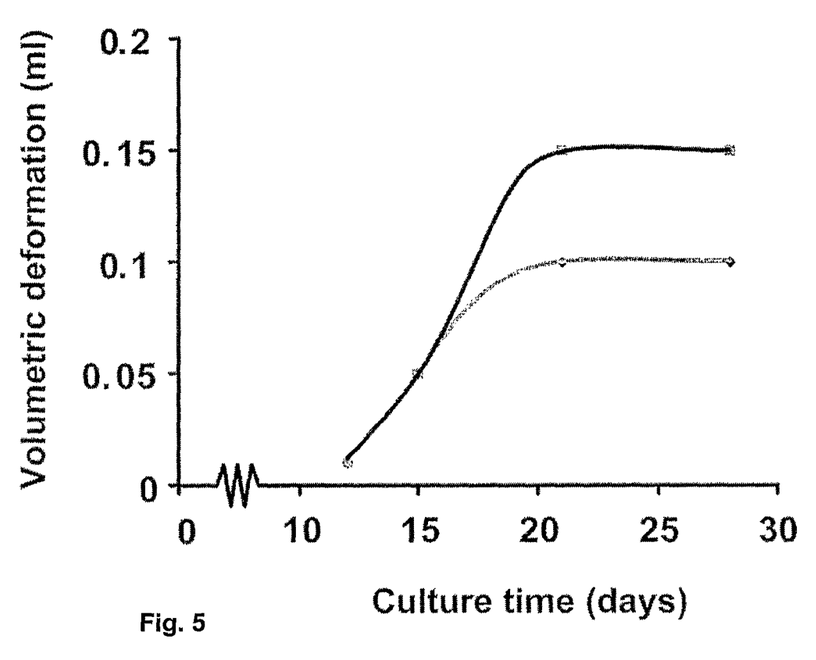
FIG. 5 depicts two predetermined mechanical conditioning protocols. These show the predetermined volumetric deformation (ml) the to be applied to the tissue-engineered heart valves. The lower deformation profile represents protocol 3 (for experiment 3) and the upper profile represents protocol 4 (for experiment 4).

Two different predetermined mechanical conditioning protocols were applied to the tissue-engineered valves in both experiments (FIG. 5). Load application was deformation controlled. The magnitude of the dynamic loads was regulated in such a way that increasing leaflet deformation values were induced from day 13 to 21 of tissue culture. At day 21, volumetric deformation was kept constant at values of 0.1 ml (protocol 1) and 0.15 ml (protocol 2) until the end of culture. In both experiments, protocol 1 was applied to heart valves A and B and protocol 2 to valves C and D.

To apply controlled diastolic loads to the cultured heart valves, the magnitudes of the applied loads were adjusted in such a way that a prescribed deformation according to protocol 1 or 2 was induced in the tissue engineered heart valve leaflets. Desired strains were obtained in the cultured valves by implementation of a deformation control loop in the bioreactor software, which controlled the pulsatile pump. This control loop allows for the adjustment of the applied load in such a way that the induced and thus measured deformations resemble the predetermined load of protocol 1 or 2. The applied load has to be adjusted during conditioning since the mechanical properties of the valve change during conditioning which influences the volumetric deformation at a certain load.

Figure 6A:
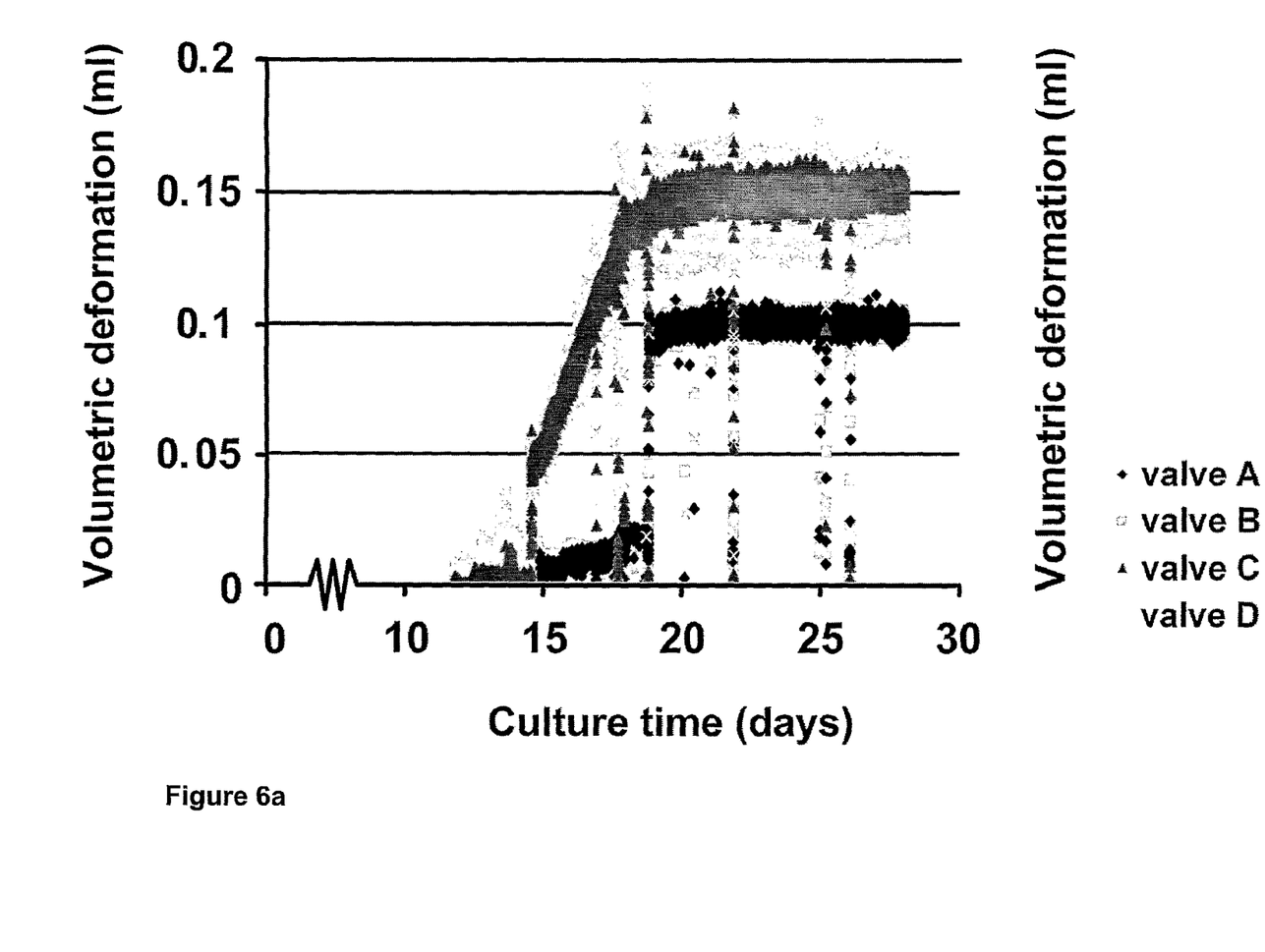
FIGS. 6a and 6b show the measured volumetric deformation values (ml) of tissue-engineered heart valves A, B, C and D, given as a function of the culture time (days) for (a) experiment 3 and (b) experiment 4.
Figure 6B:
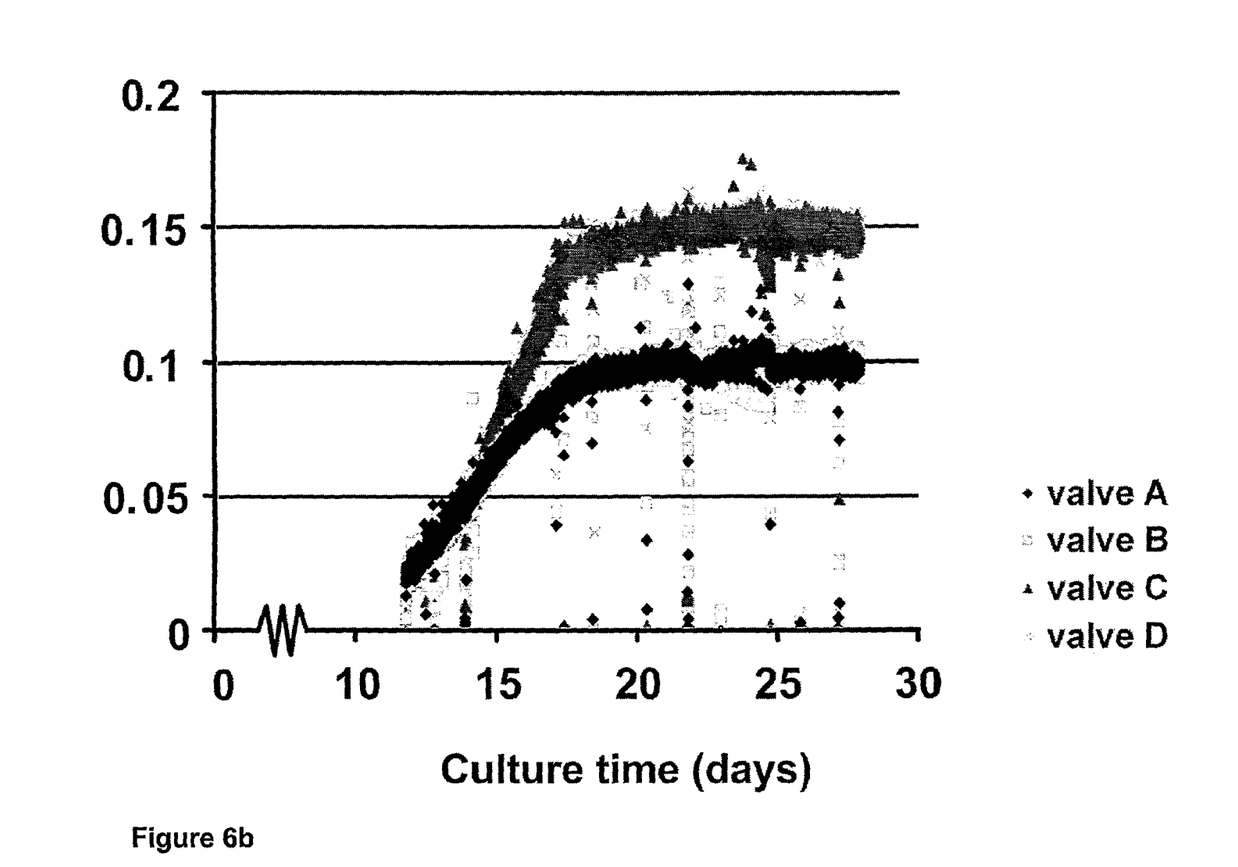

FIGS. 6a and 6b show the measured volumetric deformation during the conditioning. The measurements of FIG. 6a were obtained with conditioning protocol 1 and the measurements of 6b were obtained with conditioning protocol 2. In both applied protocols the applied load was continuously in such a way that the deformation of the valve corresponds to the prescribed deformation. Table 2 shows the relative error between the prescribed volumetric deformation and the actual measured volumetric deformation. These results show that it is possible to grow valves with a conditioning protocol which adapts the applied load to the mechanical properties of the individual valve. Together with the ability to estimate the mechanical properties of a developing and grown valve it is possible to grow a valve according to an optimal conditioning protocol, because the conditioning can be adapted to the changing mechanical properties of the valve.

TABLE 2

| Protocol | valve | Leakage (ml/min) | Young's modulus (MPa) |
|---|---|---|---|
| 1 | I-A | 0 | 0.82 |
|  | I-B | 0 | 1.14 |
|  | II-A | 3 | 1.66 |
|  | II-B | 0 | 1.07 |
| 2 | I-C | 0 | 1.22 |
|  | I-D | 5 | 1.36 |
|  | II-C | 0 | 0.77 |
|  | II-D | 3 | 1.26 |

The invention claimed is:

1. A method for manufacturing a tissue-engineered construct, the method comprising:
    providing a cell-seeded scaffold in a bioreactor chamber, which bioreactor chamber being divided by the cell-seeded scaffold into a first compartment and a second compartment;
    subjecting the cell-seeded scaffold to a flow of nutrient medium within the bioreactor chamber for developing the cell-seeded scaffold into a tissue structure to develop the tissue construct;
    applying a dynamic pressure difference to the developing tissue structure by the flow of nutrient medium to induce a volumetric deformation of the developing tissue structure and a dynamic strain on the developing tissue structure;
    measuring the dynamic pressure difference;
    measuring the volumetric deformation of the developing tissue structure;
    determining a magnitude of at least one mechanical property of the developing tissue structure based on the measured volumetric deformation and based on the applied pressure difference while the tissue structure is within the bioreactor chamber;
    determining if the determined magnitude of at least one mechanical property exceeds a threshold value;
    continuing subjection of the developing tissue structure to the flow of nutrient medium if the determined magnitude of at least one mechanical property does not exceed the threshold value; and
    ending the subjection of the developing tissue structure to the flow of nutrient medium if the determined magnitude of at least one mechanical property exceeds the threshold value, thereby resulting in the tissue-engineered construct.

2. The method of claim 1, further comprising determining local tissue strains based on the measured volumetric deformation.

3. The method of claim 2, further comprising using a numerical model to determine the magnitude of the at least one mechanical property of the tissue structure and/or the local tissue strains.

4. The method of claim 2, further comprising changing the dynamic pressure difference depending on the local tissue strains determined and/or changing the dynamic pressure difference depending on the determined magnitude of the at least one mechanical property of the developing tissue structure.

5. The method of claim 4, further comprising gradually increasing the dynamic pressure.

6. The method of claim 5, further comprising increasing the dynamic pressure to a maximum value between 10 kPa and 20 kPa.

7. The method of claim 1, further comprising the step of applying the dynamic pressure difference with a frequency between 0.1 Hz and 10 Hz.

8. The method of claim 1, further comprising applying the dynamic pressure difference for at least 6 days.

9. The method of claim 1, further comprising subjecting the cell-seeded scaffold to a continuous flow of nutrient medium at a speed between 2 ml/min and 6 ml/min to develop the cells on the cell-seeded scaffold to the developing tissue structure.

10. The method of claim 9, further comprising subjecting the cell-seeded scaffold to a continuous flow of nutrient medium in the bioreactor chamber for at least 3 days before a dynamic pressure difference is applied on the developing tissue structure.

11. The method of claim 1, wherein the tissue-engineered construct is a heart valve.

12. The method of claim 1, wherein the dynamic pressure is applied to the tissue structure which is developing to a heart valve in a closed configuration.

13. The method of claim 7, wherein the dynamic pressure is increased to a maximum value between 13 kPa and 17 kPa.

14. The method of claim 7, wherein the dynamic pressure difference is applied with a frequency between 0.5 Hz and 3 Hz.

15. The method of claim 8, wherein the dynamic pressure difference is applied for a period between 16 and 28 days.

* * * * *